US005659086A

United States Patent [19]
Pauwels et al.

[11] Patent Number: 5,659,086
[45] Date of Patent: Aug. 19, 1997

[54] PRODUCTION OF ORGANIC DISULFIDES

[75] Inventors: Alex Pauwels, Deurne, Belgium; Dean E. Stinn, Bartlesville, Okla.

[73] Assignee: Phillips Petroleum Company, Bartlesville, Okla.

[21] Appl. No.: 467,502

[22] Filed: Jun. 6, 1995

[51] Int. Cl.$^6$ ............ C07C 321/22; C07C 321/14; C07C 321/16
[52] U.S. Cl. ............ 568/26; 568/25
[58] Field of Search ............ 568/25, 26, 28

[56] References Cited

U.S. PATENT DOCUMENTS

| | | | |
|---|---|---|---|
| 2,024,567 | 12/1935 | Clifford | 260/16 |
| 2,043,949 | 6/1936 | Cramer | 260/16 |
| 2,979,532 | 4/1961 | MacGregor | 260/608 |
| 3,275,693 | 9/1966 | Bapsères . | |
| 3,994,979 | 11/1976 | Warner | 260/608 |
| 4,288,627 | 9/1981 | Kubicek | 568/26 |
| 4,868,336 | 9/1989 | Presnall | 568/25 |
| 5,202,494 | 4/1993 | Roberts et al. | 568/26 |

OTHER PUBLICATIONS

The Chemistry of Organic Sulfur Compounds (ed. N. Kharasch and C. Y. Meyers), Chapt. 8, pp. 205–232 (1966).

Organic Chemistry of Bivalent Sulfur (ed. E. E. Reid), pp. 118–119 (1958).

*Primary Examiner*—C. Warren Ivy
*Assistant Examiner*—Jean F. Vollano
*Attorney, Agent, or Firm*—Lucas K. Shay

[57] ABSTRACT

A process which can be used for producing an organic disulfide is provided. The process comprises the steps of: (1) contacting a base and a mercaptan under an effective condition for forming a brine phase comprising the base and a basic salt of a mercaptan; (2) contacting the brine phase with a mercaptan and hydrogen peroxide under a condition sufficient to effect the formation of an aqueous phase and an organic phase; (3) separating the aqueous phase from the organic phase; (4) recovering the organic phase; and optionally, (5) removing a portion of water from the aqueous phase and thereafter repeating the steps of (2) to (5).

22 Claims, No Drawings

PRODUCTION OF ORGANIC DISULFIDES

FIELD OF THE INVENTION

The present invention relates to a process for producing organic disulfides.

BACKGROUND OF THE INVENTION

Organic disulfides are a class of important industrial chemicals which can be used in the manufacture of pesticides, rodent repellants, and insecticides, as intermediates for synthesis of pharmaceuticals, and as additives in greases and fuels. High molecular weight organic disulfides can also be used as additives in the plastic industry as chain terminating agents in polymerization processes.

The production of organic disulfides is well known in the art. However, the processes currently available for producing organic disulfides, especially lower alkyl disulfides, are so tedious and expensive that the production costs remain relatively high thereby preventing real commercial development. For example, alkyl disulfides such as diethyl disulfide can be prepared from ethyl mercaptan by forming sodium ethanethiolate in either water or alcohol solution followed by oxidizing the sodium ethanethiolate with oxygen. However, the oxygen consumption is high thereby adding cost to the disulfide product. Furthermore, the yield of some organic disulfides by oxygen oxidation is generally 85% or less.

Organic disulfides can also be prepared by oxidizing mercaptans using water-soluble persulfates, perchlorates, or permanganates. However, acids are required if the oxidizing agents are perchlorates or permanganates. Additionally, the quantity of the oxidizing agents is high, generally 1 mole of oxidizing agent per 2 moles of mercaptan, in order to obtain a good yield. Use of high quantities of oxidizing agents and acids further increases manufacturing costs of organic mercaptans.

It has also been reported that mercaptans or metal salts of mercaptans can be oxidized by hydrogen peroxide in the presence of an acid. Again, such a process requires the addition of an acid thereby increasing the manufacturing costs of organic disulfides.

Therefore, there is an ever-increasing need for developing an improved and simple process for producing organic disulfides. Development of a simple process for producing organic disulfides would also significantly contribute to the art. Because the market for organic disulfides is growing larger, seemingly small improvement translates into a significant savings in manufacturing costs.

SUMMARY OF THE INVENTION

An object of the present invention is to provide a simple process for oxidizing mercaptans using hydrogen peroxide without the use of an acid. Another object of the invention is to provide a process for producing organic disulfides in high yield. A further object of the present invention is to provide a process for producing substantially pure organic disulfides. Still a further object of the present invention is to provide a process for producing an organic disulfide in near quantitative yield. Still another object of the present invention is to provide a process for producing organic disulfides which can be produced using a batch process, a continuous process, or a semicontinuous process. One of the advantages of the present invention is that the brine phase, as disclosed herein, can be reused, similar to a catalyst. Other objects, aspects, advantages, and features will become more apparent as the invention is more fully disclosed hereinbelow.

According to the present invention, a process which can be used for producing an organic disulfide is provided. The process comprises the steps of: (1) contacting a base and a mercaptan under an effective condition to form a brine phase comprising the base and a basic salt of mercaptan; (2) contacting the brine phase with a mercaptan and hydrogen peroxide under a condition sufficient to effect the formation of an organic phase and an aqueous phase; (3) separating the organic phase from the aqueous phase; (4) recovering the organic phase; and optionally, (5) removing a portion of water from the aqueous phase and thereafter repeating the steps of (2) to (5).

DETAILED DESCRIPTION OF THE INVENTION

According to the present invention, an organic disulfide having the formula of RSSR can be produced by the process of the invention wherein each R can be the same or different and is each a hydrocarbyl radical having 1 to about 30, preferably about 1 to about 20, more preferably 1 to about 10, and most preferably 1 to 5 carbon atoms. The hydrocarbyl radical can be linear or branched and can be alkyl, aryl, cycloalkyl, alkaryl, aralkyl, alkenyl radicals, or combinations of any two or more thereof. Preferably the hydrocarbyl radical is an alkyl radical.

Examples of suitable organic disulfides include, but are not limited to, dimethyl disulfide, diethyl disulfide, diisopropyl disulfide, di-n-propyl disulfide, di-n-butyl disulfide, di-t-butyl disulfide, di-n-amyl disulfide, di-t-butyl disulfide, di-t-amyl disulfide, di-n-hexyl disulfide, dicyclohexyl disulfide, didecyl disulfide, didodecyl disulfide, di-t-dodcelyl disulfide, diphenyl disulfide, dibenzyl disulfide, ditoluyl disulfide, and combinations of any two or more thereof. The presently most preferred organic disulfides are dimethyl disulfide and diethyl disulfide because the basic salts of their precursor mercaptans are readily soluble in a basic aqueous solution.

According to the first step of the present invention, any base that can form and substantially dissolve a basic salt of a mercaptan can be used. The presently preferred base can be an inorganic base, an organic base, or combinations of any two or more thereof. It is further preferred that the base be in aqueous form. Suitable organic bases include, but are not limited to, methyl amine, dimethyl amine, trimethyl amine, ethyl amine, diethyl amine, triethylamine, propyl amine, isopropyl amine, dipropyl amine, diisopropyl amine, tripropyl amine, butyl amine, tributyl amine, amyl amine, triamyl amine, hexyl amine, cyclohexyl amine, octyl amine, tetramethylammonium hydroxide, tetraethylammonium hydroxide, tetrapropylammonium hydroxide, tetramethylammonium bisulfide, tetraethylammonium bisulfide, and combinations of any two or more thereof. Suitable inorganic bases include, but are not limited to, ammonium hydroxide, lithium hydroxide, sodium hydroxide, sodium hydrosulfide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, $R^1OM$, $R^1SM$ such as sodium methanethiolate, and combinations of any two or more thereof; where $R^1$ is a $C_1$–$C_{18}$ alkyl radical, or combinations of any two or more thereof; and m is an alkali metal. Among the bases, sodium hydroxide, sodium hydrosulfide, and potassium hydroxide are preferred because they are readily available and inexpensive.

Any mercaptans that can form a basic salt with a base disclosed above and the basic salt is at least partially, preferably substantially, soluble in a basic aqueous solution and that can be converted to their corresponding disulfides can be used in the process of the present invention. The term partially soluble refers to any degree, but not substantial, solubility in a basic aqueous solution. Suitable mercaptans have the formula of RSH wherein R is the same as disclosed above. Examples of suitable mercaptans include, but are not limited to, methyl mercaptan, ethyl mercaptan, propyl mercaptan, butyl mercaptan, isopropyl mercaptan, isobutyl mercaptan, t-butyl mercaptan, amyl mercaptan, isoamyl mercaptan, hexyl mercaptan, cyclohexyl mercaptan, octyl mercaptan, nonyl mercaptan, t-nonyl mercaptan, decyl mercaptan, dodecyl mercaptan, t-dodecyl mercaptan, t-tetradodecyl mercaptan, phenyl acetyl mercaptan, p-methyl phenyl mercaptan, and combinations of any two or more thereof.

A base, if not already in aqueous form, is generally dissolved in water to form a basic aqueous solution to which a suitable mercaptan can then be added to form a brine phase. The weight percent (%) of the base can be any weight % so long as the weight % can effect the formation of the brine phase and can be in the range of from about 0.01 to about 40, preferably about 0.1 to about 30, more preferably about 1 to about 20, and most preferably 1 to 15%. The quantity of mercaptan, measured as a basic salt of mercaptan, is the quantity that can effect the formation of the brine phase and of the disulfide. Generally, the weight % of a basic salt of mercaptan is in the range of from about 0.01 to about 40, preferably about 0.1 to about 30, more preferably about 1 to about 20, and most preferably 1 to 15%. Though not required for practicing the process of the present invention, it is preferred that the weight % of basic salt of mercaptan be maintained close to about 1 weight % when reuse of the brine phase is considered in the continuous process.

Any conditions that can form a brine phase containing a base and a basic salt of mercaptan can be used for contacting a base and a mercaptan. Generally, such conditions can include a temperature in the range of from about 0° C. to about 100° C., preferably about 5° C. to about 70° C., and most preferably 10 ° C. to 50° C.; a pressure in the range of from about 0.5 to about 20, preferably about 1 to about 10, and most preferably about 1 to 5 atmospheres; and a time period sufficient to form the brine phase which is generally about 1 second to about 2 hours depending on the desired weight % of the base in the brine phase.

In the second step of the invention process, the brine phase are contacted with a mercaptan and hydrogen peroxide. The brine phase can be contacted first with a mercaptan and then with hydrogen peroxide, or first with hydrogen peroxide and then with a mercaptan. However, it is preferred that the brine phase be substantially contemporaneously contacted with both a mercaptan and hydrogen peroxide. The mole ratio of mercaptan to hydrogen peroxide can vary and can be about 2:1.

The second step of the process of the invention can be carried out under a condition sufficient to effect the formation of an aqueous phase which comprises, or consisting essentially of, or consists of a base and a basic salt of mercaptan and an organic phase which comprises, or consisting essentially of, or consists of, an organic disulfide. Suitable conditions can be the same as those disclosed above in the first step of the invention.

In the third step of the present invention, the organic phase is separated from the aqueous phase. Separation can be carried out by any methods known to one skilled in the art such as, for example, decantation, centrifugation, solvent extraction, chromatographic separation, and combinations of any two or more thereof. Because these methods are well known to those skilled in the art, the description of which is omitted herein for the interest of brevity. The presently preferred separation method is decantation because it is easy and fast for separating the phases which have large differences in density.

The separation can be carried out under any conditions that can effect the separation of the organic phase from the aqueous phase. Generally, the conditions disclosed above in the first step of the present invention can also be employed in the separation of organic phase from aqueous phase.

After the organic phase is separated from the aqueous phase, the organic phase now containing a desired organic disulfide can be recovered and marketed. The organic phase can also be further processed, if desired. For example, if the organic disulfide is contaminated with trace amount of water, the organic disulfide can be dried using a molecular sieve. The process of the invention produces a substantially pure organic disulfide, any purification process is generally not required.

The aqueous phase can be further treated to remove the excess water that is generated in and added to the brine phase by the conversion of mercaptan to disulfide and by hydrogen peroxide solution so that a desired weight % of a base and/or a basic salt of mercaptan can be obtained for the conversion of more mercaptan to disulfide using hydrogen peroxide. Water can be removed by any methods known to one skilled in the art such as, for example, distillation under a pressure.

After the excess water is removed, the brine phase now containing a base and a basic salt of a mercaptan can be used to convert a mercaptan to a disulfide by repeating the second step, third step, fourth step, and fifth step. The number of repeating these steps can be any number desired and can be about 2 to about 100 times, preferably about 2 to about 50 times, and most preferably 3 to 15 times.

As described above, the process can be carried out continuously or semicontinuously by any methods known to one skilled in the art. Because such methods are well known, description of which are omitted herein for the interest of brevity.

The following examples are provided to further assist one skilled in the art to understand the present invention and are not to be construed to unduly limit the scope of the invention process.

EXAMPLE I

This example illustrates the process of the invention for converting ethyl mercaptan to diethyl disulfide.

To a 4 liter reactor flask, initial amounts of 500 grams of 50 weight % aqueous NaOH and 935 gram of deionized water were added. The flask reactor was equipped with a reflux cooler, a mixer, and two recipient parts for addition of hydrogen peroxide and mercaptan. Then, with the cooling water circulation on the flask and the mixer in service, 125 gram of ethyl mercaptan were added to obtain a brine containing about 10.9 weight % of both the Na-ethanethiolate and free sodium hydroxide. Both concentrations were determined by potentiometric titration with HCl (1N). The two recipients on top of the reactor flask were filled with 124 gram of ethyl mercaptan (99.7 weight % purity) and the other one with 97 gram of $H_2O_2$ (35 weight %). The valves to the reactor flask were opened gradually and the ethyl mercaptan and $H_2O_2$ (35 weight %) were added slowly to the reactor under vigorous mixing, at a rate whereby the temperature was controlled at a maximum of about 40° C. This was repeated several times until the total reactor volume reached about 4 liters. In the course of this process brine samples were analyzed for salt and free caustic. Based on these results, the amounts of ethyl mercaptan and $H_2O_2$ were corrected as to follow closely the stoichiometry of the reaction and thereby avoiding the risk of excess ethyl mercaptan or $H_2O_2$ in the reactor. Then the mixer was stopped and the organic and aqueous phases were allowed to separate. Then both phases were separately removed from the reactor via the bottom drain. A total of 786 grams of diethyl disulfide was recovered representing a yield of almost 100%, based on the amount of ethyl mercaptan used. It had a purity of 99.53 weight % on capillary gas chromatography (GC). The GC analysis was conducted with a 0.32 mm×30 m capillary column packed with crosslinked methylsilicon with an initial temperature of 35° C., ramped at 15° C./min to a final temperature of 250° C. for 8 minutes. The aqueous phase was distilled at atmospheric pressure to remove 700 ml of water. The residual ethanethiolate in the brine partly moved the equilibrium back to ethyl mercaptan and NaOH. The ethyl mercaptan was lost overhead (about 50% of the sodium salt moved back to mercaptan) with the water. After distillation the brine contained 13.3 weight % caustic and 3% mercaptide. This was again transferred into the 4 liter reactor flask and 70 grams of ethyl mercaptan were added to increase the ethanethiolate concentration. Then the process continued as described above with several additions of ethyl mercaptan and $H_2O_2$. After 7 additions the reactor was allowed to phase separate. Nine hundred fifty-five (955) grams of pure (99.5 weight %) diethyl disulfide was recovered representing a near quantity yield. From the brine, 830 grams of water was removed by distillation. About half of the ethanethiolate present in the brine was lost because of the shift of equilibrium back to ethyl mercaptan. Then the process was repeated a third time. Only this time with the last addition, the $H_2O_2$ amount was increased as to reduce the ethanethiolate concentration in the brine below 1 weight %. This reduced the loss of ethyl mercaptan during the brine distillation.

EXAMPLE II

This example illustrates the conversion of methyl mercaptan to methyl disulfide using the invention process.

This run was designed so that the aqueous phase, after reaction, would contain 4% NaOH and 4% MeSNa. The initial reaction mixture contained 300 g of water; 22.2 g of NaOH; 26.7 g of methyl mercaptan; and 20 g of $H_2O_2$ (30 weight %). After the reaction as described in Example I, the aqueous layer weighed 349.1 g and the organic phase containing dimethyl disulfide (DMDS) weighed 13.0 g. The purity of the DMDS was 100%, analyzed by GC.

EXAMPLE III

This run was designed so that the aqueous phase, after reaction, would contain 10% NaOH and 10% MeSNa. The initial reaction medium contained 222.5 g of water; 55.5 g of NaOH; 66.7 g of methyl mercaptan; and 50.0 g of $H_2O_2$ (30 weight %). After the reaction, the aqueous layer weighed 346.6 g and the organic phase weighed 34.1 g. The purity of DMDS was also 100%.

EXAMPLE IV

This run was designed so that the aqueous phase, before reaction, would contain 10% NaOH and 10% MeSNa, and end with 15.1% NaOH and 0.8% MeSNa. The initial reaction medium contained 259.7 g of water; 52.7 g of NaOH; 23.0 g of methyl mercaptan; and 25.0 g of $H_2O_2$ (30 weight %). After the reaction, the aqueous phase weighed 339.7 g and the organic phase (DMDS) weighed 17.7 g. Again, the purity of DMDS was 100%.

EXAMPLE V

This run was designed so that the aqueous phase, before reaction, would contain 0% NaOH and 25.1% MeSNa. The initial reaction medium contained 365 g of water; 76.6 g of NaOH; 92.1 g of methyl mercaptan; and 100.0 g of $H_2O_2$ (30 weight %). After the reaction, the aqueous phase weighed 548.0 g and the organic phase (DMDS) weighed 74.7 g. The purity of the DMDS was 100% by GC.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed:

1. A process comprising the steps of: (1) contacting a base and an organic mercaptan under a condition sufficient to effect the formation of a brine phase comprising said base and a basic salt of an organic mercaptan; (2) contacting said brine phase with an organic mercaptan and hydrogen peroxide under a condition sufficient to effect the formation of an organic phase and an aqueous phase; (3) separating said organic phase from said aqueous phase; and (4) recovering said organic phase.

2. A process according to claim 1 wherein said base is selected from the group consisting of methyl amine, dimethyl amine, trimethyl amine, ethyl amine, diethyl amine, triethylamine, propyl amine, isopropyl amine, dipropyl amine, diisopropyl amine, tripropyl amine, butyl amine, tributyl amine, amyl amine, triamyl amine, hexyl amine, cyclohexyl amine, octyl amine, tetramethylammonium hydroxide, tetraethylammonium hydroxide, tetrapropylammonium hydroxide, tetramethylammonium bisulfide, tetraethylammonium bisulfide, ammonium hydroxide, lithium hydroxide, sodium hydroxide, sodium hydrosulfide, sodium bisulfide, potassium hydroxide, calcium hydroxide, magnesium hydroxide, sodium bicarbonate, sodium carbonate, sodium oxide, sodium sulfide, magnesium oxide, calcium oxide, calcium carbonate, sodium phenoxide, barium phenoxide, calcium phenoxide, $R^1OM$, $R^1SM$ and combinations of any two or more thereof; wherein $R^1$ is a $C_1$–$C_{18}$ alkyl radical, or combinations of any two or more thereof and M is an alkali metal.

3. A process according to claim 1 wherein said base is selected from the group consisting of sodium hydroxide, potassium hydroxide, ammonium hydroxide, and combinations of any two or more thereof.

4. A process according to claim 1 wherein said base is sodium hydroxide.

5. A process according to claim 1 wherein said mercaptan is selected from the group consisting of methyl mercaptan, ethyl mercaptan, propyl mercaptan, butyl mercaptan, isopropyl mercaptan, isobutyl mercaptan, t-butyl mercaptan, amyl mercaptan, isoamyl mercaptan, hexyl mercaptan, cyclohexyl mercaptan, octyl mercaptan, nonyl mercaptan, t-nonyl mercaptan, decyl mercaptan, dodecyl mercaptan, t-dodecyl mercaptan, t-tetradodecyl mercaptan, phenyl acetyl mercaptan, p-methyl phenyl mercaptan, and combinations of any two or more thereof.

6. A process according to claim 1 wherein said mercaptan is selected from the group consisting of methyl mercaptan, ethyl mercaptan, isopropyl mercaptan, n-propyl mercaptan, isobutyl mercaptan, n-butyl mercaptan, t-butyl mercaptan, and combinations of any two or more thereof.

7. A process according to claim 1 wherein said mercaptan is selected from the group consisting of methyl mercaptan, ethyl mercaptan, propyl mercaptan, and combinations of any two or more thereof.

8. A process according to claim 1 wherein said organic phase comprises an organic disulfide selected from the group consisting of dimethyl disulfide, diethyl disulfide, diisopropyl disulfide, di-n-propyl disulfide, di-n-butyl disulfide, di-t-butyl disulfide, di-n-amyl disulfide, di-t-butyl disulfide, di-t-amyl disulfide, di-n-hexyl disulfide, dicyclohexyl disulfide, didecyl disulfide, didodecyl disulfide, di-t-dodceyl disulfide, diphenyl disulfide, dibenzyl disulfide, ditoluyl disulfide, and combinations of any two or more thereof.

9. A process according to claim 8 wherein said disulfide is selected from the group consisting of dimethyl disulfide, diethyl disulfide, dipropyl disulfide, and combinations of any two or more thereof.

10. A process according to claim 1 further comprising the steps of: (1) removing a portion of water from said aqueous phase, after said organic phase is recovered, to from another brine phase; (2) contacting said another brine phase with a mercaptan and hydrogen peroxide under a condition sufficient to effect the formation of an organic phase and an aqueous phase; (3) separating said organic phase from said aqueous phase; and (4) recovering said organic phase; wherein said steps (1) to step (4) are repeated for about 2 to about 100 times.

11. A process according to claim 10 wherein said steps (1) to step (4) are repeated for 3 to 15 times.

12. A process for producing an organic disulfide comprising the steps of: (1) contacting a base and a mercaptan under a condition sufficient to effect the formation of a brine phase comprising said base and a basic salt of said mercaptan; (2) contacting said brine phase with said mercaptan and hydrogen peroxide under a condition sufficient to effect the formation of an organic phase and an aqueous phase; (3) separating said organic phase from said aqueous phase; (4) recovering said organic phase; (5) removing a portion of water from said aqueous phase, after said organic phase is recovered, to form another brine phase; (6) contacting said another brine phase with a mercaptan and hydrogen peroxide under a condition sufficient to effect the formation of another organic phase and another aqueous phase; (7) separating said another organic phase from said another aqueous phase; and (8) recovering said another organic phase; wherein said steps (5) to step (8) are repeated for about 2 to about 100 times.

13. A process according to claim 12 wherein said disulfide is selected from the group consisting of dimethyl disulfide, diethyl disulfide, dipropyl disulfide, and combinations of any two or more thereof.

14. A process according to claim 12 wherein said base is selected from the group consisting of sodium hydroxide, potassium hydroxide, ammonium hydroxide, and combinations of any two or more thereof.

15. A process according to claim 12 wherein said base is sodium hydroxide.

16. A process according to claim 12 wherein said mercaptan is selected from the group consisting of methyl mercaptan, ethyl mercaptan, propyl mercaptan, and combinations of any two or more thereof.

17. A process according to claim 12 wherein said disulfide is selected from the group consisting of dimethyl disulfide, diethyl disulfide, dipropyl disulfide, and combinations of any two or more thereof; said base is sodium hydroxide; said mercaptan is selected from the group consisting of methyl mercaptan, ethyl mercaptan, propyl mercaptan, and combinations of any two or more thereof; and said step (5) to step (8) are repeated for 3 to 15 times.

18. A process for producing an organic disulfide comprising the steps of: (1) contacting a base and a mercaptan under condition sufficient to effect the formation of a brine phase comprising said base and a basic salt of said mercaptan; (2) contacting said brine phase with said mercaptan and hydrogen peroxide under a condition sufficient to effect the formation of an organic phase and an aqueous phase; (3) separating said organic phase from said aqueous phase; (4) recovering said organic phase; (5) removing a portion of water from said aqueous phase, after said organic phase is recovered, to form another brine phase; (6) contacting said another brine phase with a mercaptan and hydrogen peroxide under a condition sufficient to effect the formation of another organic phase and another aqueous phase; (7) separating said another organic phase from said another aqueous phase; and (8) recovering said another organic phase; wherein:

said disulfide is selected from the group consisting of dimethyl disulfide, diethyl disulfide, dipropyl disulfide, and combinations of any two or more thereof;

said base is selected from the group consisting of sodium hydroxide, potassium hydroxide, ammonium hydroxide, and combinations of any two or more thereof;

said mercaptan is selected from the group consisting of methyl mercaptan, ethyl mercaptan, propyl mercaptan, and combinations of any two or more thereof; and said steps (5) to step (8) are repeated for about 2 to about 100 times.

19. A process according to claim 18 wherein said disulfide is dimethyl disulfide; said base is sodium hydroxide; said mercaptan is methyl mercaptan; and said step (5) to step (8) are repeated for 3 to 15 times.

20. A process according to claim 18 wherein said disulfide is diethyl disulfide; said base is sodium hydroxide; said mercaptan is ethyl mercaptan; and said step (5) to step (8) are repeated for 3 to 15 times.

21. A process according to claim 1 wherein said brine phase consists essentially of said base and a salt of a mercaptan.

22. A process according to claim 18 wherein said brine phase consists essentially of said base and a salt of a mercaptan.

* * * * *